US007833712B2

(12) United States Patent
Reeves et al.

(10) Patent No.: US 7,833,712 B2
(45) Date of Patent: *Nov. 16, 2010

(54) DIAGNOSIS AND TREATMENT OF TUMOR-SUPPRESSOR ASSOCIATED DISORDERS

(75) Inventors: Roger Harper Reeves, Silver Spring, MD (US); Yoshinori Murakami, Tokyo (JP)

(73) Assignees: The John Hopkins University School of Medicine, Baltimore, MD (US); National Cancer Center Research Institute, Tokyo (JP)

( * ) Notice: Subject to any disclaimer, the term of this patent is extended or adjusted under 35 U.S.C. 154(b) by 849 days.

This patent is subject to a terminal disclaimer.

(21) Appl. No.: 11/523,790

(22) Filed: Sep. 18, 2006

(65) Prior Publication Data

US 2007/0072224 A1    Mar. 29, 2007

Related U.S. Application Data

(60) Continuation of application No. 10/403,107, filed on Mar. 28, 2003, now Pat. No. 7,153,657, which is a division of application No. 09/930,803, filed on Aug. 15, 2001, now Pat. No. 6,596,493.

(60) Provisional application No. 60/225,264, filed on Aug. 15, 2000.

(51) Int. Cl.
*C12Q 1/68* (2006.01)

(52) U.S. Cl. .......................................... 435/6; 536/24.3
(58) Field of Classification Search ........................ None
See application file for complete search history.

(56) References Cited

U.S. PATENT DOCUMENTS 5,552,277 A   9/1996 Nelson et al. ................. 435/6

| | | | |
|---|---|---|---|
| 5,786,146 A | 7/1998 | Herman et al. | 435/6 |
| 5,856,094 A | 1/1999 | Sidransky et al. | 435/6 |
| 6,017,704 A | 1/2000 | Herman et al. | 435/6 |
| 6,200,756 B1 | 3/2001 | Herman et al. | 435/6 |
| 6,251,594 B1 | 6/2001 | Gonzalgo et al. | 435/6 |
| 6,265,171 B1 | 7/2001 | Herman et al. | 435/6 |
| 6,596,493 B1 | 7/2003 | Reeves et al. | 435/6 |
| 7,153,657 B2 * | 12/2006 | Reeves et al. | 435/6 |

OTHER PUBLICATIONS

Fukuhara et al., "Isolation of the *TSLL1* and *TSLL2* Genes, Members of the Tumor Suppressor *TSLC1* Gene Family Encoding Transmembrane Proteins." Oncogene 20:5401-5407 (2001).

Gomyo et al., "A 2-mb Sequence-ready Conting Map and a Novel Immunoglobulin Superfamily Gene IGSF4 in the LOH Region of Chromosome 11q23.2." *Genomics*, Database Gencore Accession No. AB017563, 62(2):139-146 (1999).

Kuramochi et al., " *TSLCI* is a Tumor-suppressor Gene in Human Non-Small-Cell Lung Cancer." *Nature Genetics* 27:427-430 (2001).

Murakami et al., "Localization of Tumor Suppressor Activity Important in Nonsmall Cell Lung Carcinoma on Chromosome 11q.", *Proc. Natl. Acad. Sci.* USA 95:8153-8158 (1998).

* cited by examiner

*Primary Examiner*—James S Ketter
(74) *Attorney, Agent, or Firm*—DLA Piper LLP (US)

(57) ABSTRACT

Methods are provided for detecting a cell proliferative disorder associated with TSLC1 by contacting a proliferating cell of a subject suspected of having the disorder with a reagent that detects TSLC1 and detecting the level of TSLC1 in the proliferating cell. TSLC1 is a single gene whose expression is reduced or absent in A549 and some other NSCLC, hepatocellular carcinoma and pancreatic cancer cell lines. It has further been discovered that TSLC1 expression or suppression is perfectly correlated with promoter methylation state. Restoration of TSLC1 expression to normal or higher levels is sufficient by itself to suppress tumor formation. The invention further provides methods of treating such disorders by contacting cells of a patient suffering from the disorder with a therapeutically effective amount of a reagent that modulates TSLC1 level in the proliferating cells.

18 Claims, 7 Drawing Sheets

5'- GTGAGTGACGGAAATTTGCAA

CGTCTGGTTCGCTAGGCCAGAT
          1

GCACTCGGTGTCGGGACAGAG
      2      3

GACCCTCTTAAGGGAGATTCTC

CAGT CGTCGGTCTGATACAGCG
      4  5              6

ATTGCTATAAACATTCCTAATA

AAGGTGTACAAGAAGCTAGACC-3'

FIGURE 2C

|  | CpG site | TSLC1 expression |
|---|---|---|
|  | 1 2 3 4 5 6 |  |
| normal lung | ○○○○○○ | + |
| SK-LU-1 | ●●●●●● | − |
| Calu-3 | ●●●●●● | − |
| NCI-H596 | ◉◉◉◉◉◉ | − |
| PC-14 | ◉◉◉◉◉◉ | − |
| A549 | ○○○○○○ | +/− |
| A431 | ○○○○○○ | +/− |
| ABC-1 | ○○○○○○ | + |
| NCI-H441 | ○○○○○○ | + |
| NCI-H522 | ○○○○○○ | + |
| LCMS | ○○○○○○ | + |
| LCOK | ○○○○○○ | + |
| VMRC-LCD | ○○○○○○ | + |

FIGURE 2E

DIAGNOSIS AND TREATMENT OF TUMOR-SUPPRESSOR ASSOCIATED DISORDERS

This application is a continuation application of U.S. application Ser. No. 10/403,107 filed Mar. 28, 2003 now U.S. Pat. No. 7,153,657; which is a divisional application of U.S. application Ser. No. 09/930,803 filed Aug. 15, 2001, now issued as U.S. Pat. No. 6,596,493; which claims priority under 35 U.S.C. §119(e) of U.S. application Ser. No. 60/225,264, filed Aug. 15, 2000, now abandoned. The disclosure of each of the prior applications is considered part of and is incorporated by reference in the disclosure of this application.

This invention was made in part with government support under Grant No. 2P01HD24605 awarded by the National Institutes of Health and U.S. Public Health Service award HD-24605. The government may have certain rights in this invention.

BACKGROUND OF THE INVENTION

1. Field of the Invention

The invention relates generally to screening assays and molecular medicine, and more specifically to methods for identifying individuals having or at risk of developing cancer, for grading the severity and determining the prognosis of such cancers, and for treating or preventing such cancers.

2. Background Information

Lung cancer is the leading cause of cancer death, and 80% of lung cancers are non-small cell lung cancer (NSCLC). While human lung cancer is not thought of as a genetic disease, a variety of molecular genetic studies have shown that lung cancer cells have acquired a number of genetic lesions including activation of dominant oncogenes and inactivation of tumor suppressor or recessive oncogenes. In fact, it appears that to become clinically evident, lung cancer cells have to accumulate a large number (perhaps 10 or more) of such lesions. For the dominant oncogenes, these include point mutations in the coding regions of the ras family of oncogenes (particularly in the K-ras gene in adenocarcinoma of the lung) and amplification, rearrangements, and/or loss of transcriptional control of myc family oncogenes (c-, N-, and L-myc), with changes in c-myc found in non-small cell cancers while changes in all myc family members are found in small cell lung cancer. Tumor mutations in ras genes are associated with poor prognosis in non-small cell lung cancer, while tumor amplification of c-myc is associated with poor prognosis in small cell lung cancer.

For the recessive oncogenes (tumor suppressor genes), cytogenetic and restriction fragment length polymorphism (RFLP) analyses have shown deletions (allele loss) involving chromosome regions 1p, 1q, 3p14, 3p21, 3p24-25, 3q, 5q (familial polyposis gene cluster), 9p (interferon gene cluster), 11p, 13q14 (retinoblastoma, rb, gene) 16q, and 17p13 (p53 gene), as well as other sites. There appear to be several candidate recessive oncogenes on chromosome 11q that are involved in nearly all lung cancers.

The large number of genetic lesions in clinically evident lung cancer has prompted a search for these mutations in lung tissue before classic cytopathologic evidence of malignancy can be found, to provide for molecular early diagnosis and as intermediate endpoints in prevention efforts, including chemo-prevention treatment.

Pancreatic cancer is the fourth leading cause of cancer death in men and in women and each year ~28,000 Americans die of the disease (6). Frequent genetic changes such as mutational activation of the K-ras oncogene and inactivation of the p16, DPC4, p53, MKK4, STK11, TGFBR2, and TGFBR1 tumor suppressor genes have been described in pancreatic cancer (7, 8). Although multiple tumor suppressor pathways have been shown to play a role in pancreatic carcinogenesis, little is known about the contribution of DNA methylation to inactivation of genes in these pathways. Recently, a novel technique, methylated CpG island amplification (MCA), was developed to enrich for methylated CpG rich sequences. MCA coupled with RDA (MCA/RDA) can recover CpG islands differentially methylated in cancer cells.

Primary hepatocellular carcinoma is one of the most common tumors in the world. It is especially prevalent in regions of Asia and sub-Saharan Africa, where the annual incidence is up to 500 cases per 1000,000 population. In the United States and western Europe, it is much less common, accounting for only 1 to 2 percent of malignant tumors at autopsy. Hepatocellular carcinoma is up to four times for common in men than in women and usually arises in a cirrhotic liver.

The principal reason for the high incidence of hepatocellular carcinoma in parts of Asia and Africa is the frequency of chronic infection with hepatitis B virus (HBV) and hepatitis C virus (HBC). These chronic infections frequently lead to chirrhosis, which itself is an important risk factor for hepatocellular cancinomas. In patients with HBV infection and hepatocellular carcinoma, there can be modifications of cellular gene expression by insertional mutagenesis, chromosomal rearrangements, or the transcriptional transactivating activity of the X and the pre-52/S regions of the HBV genome. These alternations probably occur during the process of liver cell injury and repair.

Thus, there is a need in the art for new and better methods for diagnosing individuals having or at risk of developing lung, liver and pancreatic cancers as well as a need for methods of treatment of such conditions.

SUMMARY OF THE INVENTION

The present invention is based on the seminal discovery that a region of 700 kb on 11q23.2 can suppress tumorigenicity of A549 human non-small cell lung cancer (NSCLC) cells, as well as some other NSCLC, hepatocellular carcinoma (HCC) and pancreatic cancer (PAC) cell lines. Accordingly, the present invention provides methods of detecting a cell proliferative disorder associated with tumor suppressor lung cancer 1 (TSLC1) in a subject in need thereof by contacting a cell component of a proliferating cell of the subject with a reagent that detects the level of the cell component in the proliferating cell and determining a modification in the level of the cell component in the proliferating cell as compared with a comparable healthy cell, wherein the cell component indicates the level of TSLC1 in the cell and the modification indicates the disorder associated with TSLC1.

In another embodiment, the present invention provides methods of detecting a cell proliferative disorder in a subject in need thereof by contacting a target cellular component of a test cell with a reagent that detects the level of TSLC1 and detecting a reduction in the level of TSLC1 in the proliferating cell as compared to that of a comparable normal cell; wherein the cell proliferative disorder is a TSLC1-associated lung, liver or pancreatic cancer.

In yet another embodiment, the present invention provides methods of treating a cell proliferative disorder associated with modification of TSLC1 production in proliferating cells in a subject in need thereof. In the invention therapeutic methods, cells of a patient suffering from such a disorder are contacted with a therapeutically effective amount of a reagent that modulates TSLC1 level in the proliferating cells.

BRIEF DESCRIPTION OF THE DRAWINGS

FIG. 2C shows the sequence of a CpG island upstream from TSLC1 (SEQ ID NO:24) (with nucleic acids 62-79 boxed). Primer sequences used to amplify this region are underlined and CpG sites, number 1-6, are doubly underlined. Predicted TATA box sequence is shown with a dashed underline.

FIG. 2E is a chart showing the methylation status of the TSLC1 promoter in a normal lung and 12 NSCLC cell lines. White and black circles represent unmethylated and methylated CpGs, respectively. Grey circles represent partially methylated CpGs. Columns correspond to the six identified sites of methylated cytosine residues in CpG sites shown in FIG. 2D.

DETAILED DESCRIPTION OF THE INVENTION

Figure 1A:
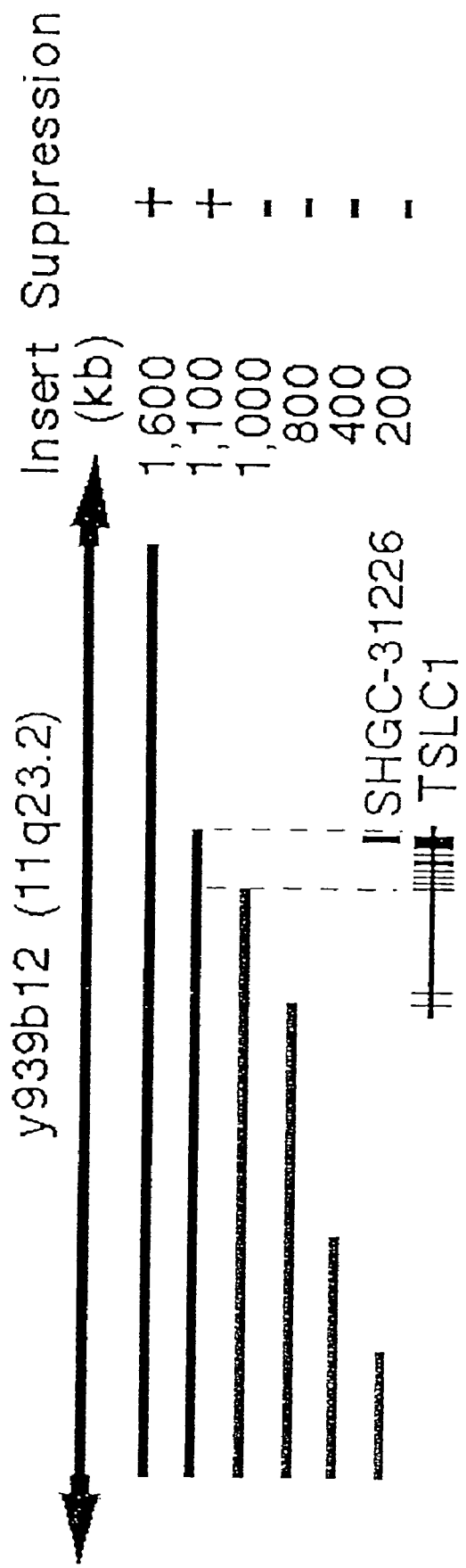
FIG. 1A is a schematic representation of DNA segments used for functional mapping of tumor suppressor activity of TSLC1 using 1.6 MB YAC and nested deletion derivatives of it transfected into A549 NSCLC tumor cells. TSLC1 was localized to a 100 kb segment responsible essential for full suppression. SHGC-31226 is an EST clone mapped on y939b12. (B) Variable expression of TSLC1 in human tissues.

The present invention is based on the seminal discovery that a region of 700 kb on 11q23.2 can suppress tumorigenicity of A549 human non-small cell lung cancer (NSCLC) cells, as well as some other NSCLC, hepatocellular carcinoma (HCC) and pancreatic cancer (PAC) cell lines. Most of this tumor suppressor activity localizes to a 100 kb segment. This region contains a single gene, TSLC1 (bases 25 through 1353 of a polynucleotide available as DNA Data Base of Japan (DDBJ) Accession No. AB017563) (SEQ ID NO:2), whose expression is reduced or absent in A549 and some other NSCLC, hepatocellular carcinoma and pancreatic cancer cell lines. It has further been discovered that TSLC1 expression or suppression is perfectly correlated with promoter methylation state. Restoration of TSLC1 expression to normal or higher levels is sufficient by itself to suppress tumor formation by A549 cells in nude mice. These results, and the identification of truncating mutations uncovered by loss of the wild type allele detected in a primary lung and a liver tumor, suggest that attenuation of TSLC1 expression is involved in multiple human cancers.

Accordingly, the present invention provides methods of detecting a cell proliferative disorder associated with tumor suppressor lung cancer 1 (TSLC1) in a subject in need thereof by contacting a cell component of a proliferating cell of the subject with a reagent that detects the level of the cell component in the proliferating cell and determining a modification in the level of the cell component in the proliferating cell as compared with a comparable healthy cell, wherein the cell component indicates the level of TSLC1 in the cell and the modification indicates the disorder associated with TSLC1. The target cell component contacted can be nucleic acid, such as DNA or RNA, or it can be protein. When the component is nucleic acid, the reagent is typically a nucleic acid probe or PCR primer. When the cell component is protein, the reagent is typically an anti-TSLC1 antibody probe. The target cell component may be detected directly in situ or it may be isolated from other cell components by common methods known to those of skill in the art before contacting with a probe. (See for example, Maniatis, et al., *Molecular Cloning, A Laboratory Manual*, Cold Spring Harbor Laboratory, N.Y., 1989; *Current Protocols in Molecular Biology*, 1994, Ed. Ausubel, et al., Greene Publ. Assoc. & Wiley Interscience.)

Detection methods include Southern and Northern blot analyses, RNase protection, immunoassays and other detection assays that are known to those of skill in the art.

The probes can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probes or will be able to ascertain such, using routine experimentation.

Since the present invention shows that a decreased level of TSLC1 transcription is often the result of hypermethylation of the TSLC1 gene, it is often desirable to directly determine whether the TSLC1 gene is hypermethylated. In particular, the cytosine rich areas termed "CpG islands," which lie in the 5' regulatory regions of genes are normally unmethylated. The term "hypermethylation" includes any methylation of cytosine at a position that is normally unmethylated in the TSLC1 gene sequence (e.g. the TSLC1 promoter). Hypermethylation can be detected by restriction endonuclease treatment of TSLC1 polynucleotide (gene) and Southern blot analysis for example. Therefore, in an invention method wherein the cellular component detected is DNA, restriction endonuclease analysis is preferable to detect hypermethylation of the TSLC1 gene. Any restriction endonuclease that includes CG as part of its recognition site and that is inhibited when the C is methylated, can be utilized. Methylation sensitive restriction endonucleases such as BssHII, MspI, NotI or HpaII, used alone or in combination, are examples of such endonucleases. Other methylation sensitive restriction endonucleases will be known to those of skill in the art. In addition, PCR can be utilized to detect the methylation status of the TSLC1 gene. Oligonucleotide primers based on any coding sequence region in the TSLC1 sequence are useful for amplifying DNA by PCR in the invention methods.

For purposes of the invention, an antibody (i.e., an anti-TSLC1 antibody) or nucleic acid probe specific for TSLC1 may be used to detect the presence of TSLC1 polypeptide (using antibody) or polynucleotide (using nucleic acid probe) in biological fluids or tissues. Oligonucleotide primers based on any coding sequence region in the TSLC1 sequence are useful for amplifying DNA, for example by PCR. Any specimen containing a detectable amount of TSLC1 polynucleotide or TSLC1 polypeptide antigen can be used. Nucleic acid can also be analyzed by RNA in situ methods that are known to those of skill in the art and illustrated in the Examples contained herein. Preferred tissues for testing or treating according to the invention methods are tissue of lung, pancreas, liver, and the like. Although the subject can be any mammal, preferably the subject is human.

Various disorders that are detectable by the method of the invention include non-small cell lung cancer, hepatocellular carcinoma, pancreatic cancer, and the like.

The invention methods can utilize antibodies immunoreactive with TSLC1 polypeptide (SEQ ID NO:1) (a predicted amino acid sequence available as GenBak Accession No. BAA75822) or immunoreactive fragments thereof. Antibody that consists essentially of pooled monoclonal antibodies with different epitopic specificities, as well as distinct monoclonal antibody preparations can be used. Monoclonal antibodies are made from antigen containing fragments of the protein by methods well known to those skilled in the art (Kohler, et al., *Nature*, 256:495, 1975). The term antibody as used in this invention is meant to include intact molecules as well as fragments thereof, such as Fab and F(ab')$_2$, which are capable of binding an epitopic determinant on TSLC1.

Monoclonal antibodies can be used in the invention diagnostic methods, for example, in immunoassays in which they can be utilized in liquid phase or bound to a solid phase carrier. In addition, the monoclonal antibodies in these immunoassays can be detectably labeled in various ways. Examples of types of immunoassays that can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays that are run in either the forward, reverse, or simultaneous modes, including immunohistochemical assays on physiological samples. Those of skill in the art will know, or can readily discern, other immunoassay formats without undue experimentation.

The term "immunometric assay" or "sandwich immunoassay", includes simultaneous sandwich, forward sandwich and reverse sandwich immunoassays. These terms are well understood by those skilled in the art. Those of skill will also appreciate that antibodies according to the present invention will be useful in other variations and forms of assays that are presently known or which may be developed in the future. These are intended to be included within the scope of the present invention.

Monoclonal antibodies can be bound to many different carriers and used to detect the presence of TSLC1. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-TSLC1 immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i.e., nonspecific) antibodies of the same class or subclass (isotype) as those used in the assays (e.g., IgG1, IgG2a, IgM, etc.) can be used as "blockers". The concentration of the "blockers" (normally 1-100 µg/µl) may be important, in order to maintain the proper sensitivity yet inhibit any unwanted interference by mutually occurring cross-reactive proteins in the specimen.

In using a monoclonal antibody for the in vivo detection of antigen, the detectably labeled monoclonal antibody is given in a dose that is diagnostically effective. The term "diagnostically effective" means that the amount of detectably labeled monoclonal antibody is administered in sufficient quantity to enable detection of the site having the TSLC1 antigen for which the monoclonal antibodies are specific. The concentration of detectably labeled monoclonal antibody which is administered should be sufficient such that the binding to those cells having TSLC1 is detectable compared to the background, depending upon the in vivo imaging or detection method employed, such as MRI, CAT scan, and the like. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors known to those of skill in the art.

For in vivo diagnostic imaging, the type of detection instrument available is a major factor in selecting a given radioisotope. The radioisotope chosen must have a type of decay that is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140-250 keV range, which may be readily detected by conventional gamma cameras.

For in vivo diagnosis, radioisotopes can be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions that can be bound to the monoclonal antibodies of the invention are $^{111}$In, $^{97}$Ru, $^{67}$Ga, $^{68}$Ga, $^{72}$As, $^{89}$Zr, and $^{201}$Tl.

A monoclonal antibody useful in the invention methods can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements that are particularly useful in such techniques include $^{157}$Gd, $^{55}$Mn, $^{162}$Dy, $^{52}$Cr, and $^{56}$Fe.

The present invention also provides methods for treating a subject with a cell proliferative disorder associated with TSLC1 comprising administering to a subject with the disorder a therapeutically effective amount of a reagent that modulates TSLC1 expression. In non-small lung cancer, hepatocellular carcinoma and pancreatic cancer cells, for example, the TSLC1 nucleotide sequence is under-expressed as compared to expression in a normal cell, therefore, it is possible to design appropriate therapeutic or diagnostic techniques directed to this sequence. Thus, where a cell-proliferative disorder is associated with the expression of TSLC1 associated with malignancy, nucleic acid sequences that modulate TSLC1 expression at the transcriptional or translational level can be used. In cases when a cell proliferative disorder or abnormal cell phenotype is associated with the under expression of TSLC1, for example, nucleic acid sequences encoding TSLC1 (sense) could be administered to the subject with the disorder.

The term "cell-proliferative disorder" denotes malignant as well as non-malignant cell populations, which often appear to differ from the surrounding tissue both morphologically and genotypically. Such disorders may be associated, for example, with absence of or reduced expression of TSLC1. Essentially, any disorder that is etiologically linked to expression of TSLC1 could be considered susceptible to treatment using invention methods that employ a reagent of the invention to modulate TSLC1 expression.

The term "modulate" encompasses the suppression of methylation of TSLC1 polynucleotide when TSLC1 is underexpressed. When a cell proliferative disorder is associated with TSLC1 expression, such methylation suppressive reagents as 5-azacytadine can be introduced to a cell. Alternatively, when a cell proliferative disorder is associated with under-expression of TSLC1 polypeptide, a sense polynucleotide sequence (the DNA coding strand) encoding TSLC1 polypeptide, or 5' regulatory nucleotide sequences (i.e., promoter) of TSLC1 in operable linkage with TSLC1 polynucleotide can be introduced into the cell. Demethylases known in the art could also be used to remove methylation.

The present invention also provides gene therapy for the treatment of cell proliferative disorders that are mediated by TSLC1. Such therapy would achieve its therapeutic effect by introduction of the appropriate TSLC1 polynucleotide that contains a TSLC1 structural gene (sense), into cells of subjects having the proliferative disorder. Delivery of sense TSLC1 polynucleotide constructs can be achieved using a recombinant expression vector such as a chimeric virus or a colloidal dispersion system.

The polynucleotide sequences used in the methods of the invention may be the native, unmethylated sequence or, alternatively, may be a sequence in which a nonmethylatable analog is substituted within the sequence. Preferably, the analog is a nonmethylatable analog of cytidine, such as 5-azacytadine. Other analogs will be known to those of skill in the art. Alternatively, such nonmethylatable analogs could be administered to a subject as drug therapy, alone or simultaneously with a sense structural gene for TSLC1 or sense promoter for TSLC1 operably linked to TSLC1 structural gene.

In another embodiment, a TSLC1 structural gene is operably linked to a tissue specific heterologous promoter and used for gene therapy. For example, a TSLC1 gene can be ligated to hepatocellular-specific promoter for expression of TSLC1 in hepatocellular tissue. Other tissue specific promoters will be known to those of skill in the art. Alternatively, the promoter for another tumor suppressor gene can be linked to the TSLC1 structural gene and used for gene therapy.

Various viral vectors that can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Most preferably, a non-human primate retroviral vector is employed, such as the gibbon ape leukemia virus (GaLV), thereby providing a broader host range than murine vectors, for example.

A number of additional retroviral vectors can incorporate multiple genes. All of these vectors can transfer or incorporate a gene for a selectable marker so that transduced cells can be identified and generated. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the TSLC1 sense or antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include but are not limited to PSI2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Another targeted delivery system for TSLC1 polynucleotide is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles that are useful as delivery vehicles in vitro and in vivo. It has been shown that large unilamellar vesicles (LUV), which range in size from 0.2-4.0 um, can encapsulate a substantial percentage of aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal-targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest that will bind to another compound, such as a receptor.

In general, surface membrane proteins that bind to specific effector molecules are referred to as receptors. In the present invention, antibodies are preferred receptors. Antibodies can be used to target liposomes to specific cell-surface ligands. For example, certain antigens expressed specifically on tumor cells, referred to as tumor-associated antigens (TAAs), may be exploited for the purpose of targeting TSLC1 antibody-containing liposomes directly to the malignant tumor. Since the TSLC1 gene product may be indiscriminate with respect to cell type in its action, a targeted delivery system offers a significant improvement over randomly injecting non-specific liposomes. Preferably, the target tissue is human brain, colon, breast, lung, and renal origin. A number of procedures can be used to covalently attach either polyclonal or monoclonal antibodies to a liposome bilayer. Antibody-targeted liposomes can include monoclonal or polyclonal antibodies or fragments thereof such as Fab, or F(ab')$_2$, as long as they bind efficiently to an antigenic epitope on the target cells. Liposomes may also be targeted to cells expressing receptors for hormones or other serum factors.

For use in the diagnostic research and therapeutic applications suggested above, kits are also provided by the invention. Such a kit may comprise a carrier means being compartmentalized to receive in close confinement one or more container means such as vials, tubes, and the like, each of the container means comprising one of the separate elements to be used in the method.

For example, one of the container means may comprise a probe that is or can be detectably labeled. Such probe may be an antibody or nucleotide specific for a target protein or a target nucleic acid, respectively, wherein the target is indicative, or correlates with, the presence of TSLC1 of the invention. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radionucleotide label.

The invention methods utilize a functional polypeptide, TSLC1, and functional fragments thereof. As used herein, the term "functional polypeptide" refers to a polypeptide that possesses a biological function or activity which is identified through a defined functional assay and which is associated with a particular biologic, morphologic, or phenotypic alteration in the cell. Functional fragments of the TSLC1 polypeptide include fragments of TSLC1 that retain the activity of e.g., tumor suppressor activity, of TSLC1. Smaller peptides containing the biological activity of TSLC1 are included in the invention. The biological function, for example, can vary from a polypeptide fragment as small as an epitope to which an antibody molecule can bind to a large polypeptide that is capable of participating in the characteristic induction or programming of phenotypic changes within a cell.

The invention methods can also utilize a "functional polynucleotide" denotes a polynucleotide which encodes a functional TSLC1 polypeptide as described herein.

Minor modifications of the TSLC1 primary amino acid sequence may result in proteins that have substantially equivalent activity as compared to the TSLC1 polypeptide described herein. Such modifications may be deliberate, as by site-directed mutagenesis, or may be spontaneous. All of the polypeptides produced by these modifications are included herein as long as the tumor suppressor activity of TSLC1 is present. Further, deletion of one or more amino acids can also result in a modification of the structure of the resultant molecule without significantly altering its activity. This can lead to the development of a smaller active molecule that would have broader utility. For example, it possible to remove amino or carboxy terminal amino acids that may not be required for TSLC1 activity.

The TSLC1 polypeptide used in the invention methods or encoded by polynucleotides used in the invention methods also includes conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention methods also can utilize an isolated polynucleotide sequence consisting essentially of a polynucleotide sequence encoding a polypeptide having the amino acid sequence of SEQ ID NO:1. The polynucleotide sequence may also includes the 5' and 3' untranslated sequences and regulatory sequences, for example. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences that encode TSLC1. It is understood that all polynucleotides encoding all or a portion of TSLC1 can also be used in the invention methods, as long as they encode a polypeptide with TSLC1 activity. For example, the polynucleotide can be a nucleic acid probe having a nucleotide sequence a) as set forth in nucleic acid residues 411-1,371 of cDNA encoding TSLC1 (SEQ ID NO:17), b) a polynucleotide having at least 70% identity or complementary to such a polynucleotide, or a polynucleotide comprising at least 15 bases of a polynucleotide of a) or b).

Such polynucleotides include naturally occurring, synthetic, and intentionally manipulated polynucleotides. For example, TSLC1 polynucleotide may be subjected to site-directed mutagenesis. The polynucleotide sequence for TSLC1 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of TSLC1 polypeptide encoded by the nucleotide sequence is functionally unchanged. In addition, the invention also includes a polynucleotide consisting essentially of a polynucleotide sequence encoding a polypeptide having an amino acid sequence of SEQ ID NO:3 and having at least one epitope for an antibody immunoreactive with TSLC1 polypeptide.

"Identity" refers to sequence similarity between two peptides or between two nucleic acid molecules. Homology can be determined by comparing a position in each sequence that may be aligned for purposes of comparison. When a position in the compared sequence is occupied by the same base or amino acid, then the molecules are homologous at that position. A degree of homology between sequences is a function of the number of matching or homologous positions shared by the sequences.

The term "transfection" or "transforming" and grammatical equivalents thereof, refers to the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of one of the invention family of TSCL1 tumor suppressors.

"Cells" or "cell cultures" or "recombinant host cells" or "host cells" are often used interchangeably as will be clear from the context. These terms include the immediate subject cell that expresses the tumor suppressor protein of the present invention, and, of course, the progeny thereof. It is understood that not all progeny are exactly identical to the parental cell, due to chance mutations or difference in environment. However, such altered progeny are included in these terms, so long as the progeny retain the characteristics relevant to those conferred on the originally transformed cell. In the present case, such a characteristic might be the ability to produce a recombinant TSCL1 tumor suppressor polypeptide.

DNA sequences used in the invention methods can be obtained by several methods. For example, the DNA can be isolated using hybridization techniques that are well known in the art. These include, but are not limited to: 1) hybridization of genomic or cDNA libraries with probes to detect homologous nucleotide sequences and 2) antibody screening of expression libraries to detect cloned DNA fragments with shared structural features.

Preferably the TSLC1 polynucleotide used in the invention methods is derived from a mammalian organism, and most preferably from human. Oligonucleotide probes, which correspond to a part of the sequence encoding the protein in question, can be synthesized chemically for use in the invention methods. This requires that short, oligopeptide stretches of amino acid sequence must be known. The DNA sequence encoding the protein can be deduced from the genetic code; however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res., 9:879, 1981).

Specific DNA sequences encoding TSLC1 for use in the invention methods can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries that are derived from reverse transcription of mRNA that is abundant in donor cells that have a high level of gene expression. When used in combination with polymerase chain reaction technology, even rare expression products can be cloned, as is illustrated in the Examples herein. In those cases where significant portions of the amino acid sequence of the polypeptide are known, the production of labeled single or double-stranded DNA or RNA sequences duplicating a sequence putatively present in the target cDNA may be employed in DNA/DNA hybridization procedures which are carried out on cloned copies of the cDNA which have been denatured into a single-stranded form (Jay, et al., Nucl. Acid Res., 11:2325, 1983).

A cDNA expression library, such as lambda gt11, can be screened indirectly to obtain TSLC1 peptides having at least one epitope, using antibodies specific for TSLC1. Such antibodies can be either polyclonally or monoclonally derived and used to detect expression product indicative of the presence of TSLC1 cDNA in a test suspected of being a proliferating cell.

DNA sequences encoding TSLC1 can be expressed in vitro by DNA transfer into a suitable host cell, such as a tumor cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the TSLC1 polynucleotide sequences may be inserted into a recombinant expression vector for expression either in vivo or in vitro. The term "recombinant expression vector" refers to a plasmid, virus or other vehicle known in the art that has been manipulated by insertion or incorporation of the TSLC1 genetic sequences. Such expression vectors contain a promoter sequence that facilitates the efficient transcription of the inserted genetic sequence of the host. The expression vector typically contains an origin of replication, a promoter, as well as specific genes that allow phenotypic selection of the transformed cells. Vectors suitable for use in the present invention include, but are not limited to the T7-based expression vector for expression in bacteria (Rosenberg, et al., *Gene* 56:125, 1987), the pMSXND expression vector for expression in mammalian cells (Lee and Nathans, *J. Biol. Chem.,* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding TSLC1 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Methods that are well known to those skilled in the art can be used to construct expression vectors containing the TSLC1 coding sequence and appropriate transcriptional/translational control signals. These methods include in vitro recombinant DNA techniques, synthetic techniques, and in vivo recombination/genetic techniques. See, for example, the techniques described in Maniatis, et al., 1989 *Molecular Cloning A Laboratory Manual*, Cold Spring Harbor Laboratory, N.Y.

A variety of host-expression vector systems may be utilized to express the TSLC1 coding sequence. These include but are not limited to microorganisms such as bacteria transformed with recombinant bacteriophage DNA, plasmid DNA or cosmid DNA expression vectors containing the TSLC1 coding sequence; yeast transformed with recombinant yeast expression vectors containing the TSLC1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the TSLC1 coding sequence; insect cell systems infected with recombinant virus expression vectors (e.g., baculovirus) containing the TSLC1 coding sequence; or animal cell systems infected with recombinant virus expression vectors (e.g., retroviruses, adenovirus, vaccinia virus) containing the TSLC1 coding sequence, or transformed animal cell systems engineered for stable expression. Since TSLC1 has not been confirmed to contain carbohydrates, both bacterial expression systems as well as those that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter, et al., *Methods in Enzymology* 153:516-544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted TSLC1 coding sequence. In addition, the endogenous TSLC1 promoter, or a mutation thereof to protect the promoter from hypermethylation, may also be used to provide transcription machinery of TSLC1.

When the expression vector is introduced into a mammalian host cell in practice of the invention methods, a eukaryotic systems, and preferably mammalian expression systems, allows for proper post-translational modifications of expressed mammalian proteins to occur. Eukaryotic cells which possess the cellular machinery for proper processing of the primary transcript, glycosylation, phosphorylation, and advantageously, secretion of the gene product may be used as host cells for the expression of TSLC1.

Recombinant viruses or viral elements may be used to direct expression in mammalian cells. For example, when using adenovirus expression vectors, the TSLC1 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the protein in infected host cells (e.g., see Logan & Shenk, *Proc. Natl. Acad Sci. USA,* 81:3655-3659, 1984). Alternatively, the vaccinia virus 7.5K promoter may be used (e.g., see, Mackett, et al., 1982, *Proc. Natl. Acad. Sci. USA* 79:7415-7419; Mackett, et al., *J. Virol.* 49:857-864, 1984; Panicali, et al., *Proc. Natl. Acad. Sci. USA* 79:4927-4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the TSLC1 gene in mammalian host cells (Cone & Mulligan, *Proc. Natl. Acad. Sci. USA* 81:6349-6353, 1984.

For long-term, high-yield production of recombinant proteins, as in gene therapy, stable expression is preferred. Rather than using expression vectors that contain viral origins of replication, host cells can be transformed with the TSLC1 cDNA controlled by appropriate expression control elements (e.g., promoter, enhancer, sequences, transcription terminators, polyadenylation sites, etc.), and, optionally, a selectable marker. The selectable marker in the recombinant plasmid confers resistance to the selection and allows cells to stably integrate the plasmid into their chromosomes and grow to form foci that in turn can be cloned and expanded into cell lines. For example, following the introduction of foreign DNA, engineered cells may be allowed to grow for 1-2 days in an enriched media, and then are switched to a selective media. A number of selection systems may be used, including but not limited to the herpes simplex virus thymidine kinase (Wigler, et al., *Cell*, 11:223, 1977), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., *Cell*, 22: 817, 1980) genes can be employed in tk⁻, hgprt⁻ or aprt⁻ cells respectively. Also, antimetabolite resistance can be used as the basis of selection for dhfr, which confers resistance to methotrexate (Wigler, et al., *Natl. Acad. Sci. USA*, 77:3567, 1980; O'Hare, et al., *Proc. Natl. Acad. Sci. USA*, 78: 1527, 1981); gpt, which confers resistance to mycophenolic acid (Mulligan & Berg, *Proc. Natl. Acad Sci. USA*, 78: 2072, 1981; neo, which confers resistance to the aminoglycoside G-418 (Colberre-Garapin, et al., *J. Mol. Biol*, 150:1, 1981); and hygro, which confers resistance to hygromycin (Santerre, et al., *Gene*, 30:147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA*, 85:8047, 1988); and ODC (omithine decarboxylase), which confers resistance to the omithine decarboxylase inhibitor, 2-(difluoromethyl)-DL-ornithine, DFMO (McConlogue L., 1987, In: *Current Communications in Molecular Biology*, Cold Spring Harbor Laboratory, ed.).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the CaCl.sub.2 method using procedures well known in the art. Alternatively, MgCl$_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the TSLC1 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman, ed., 1982).

Isolation and purification of microbial or host cell expressed polypeptide, or fragments thereof, provided by the invention, may be carried out by conventional means including preparative chromatography and affinity and immunological separations involving monoclonal or polyclonal antibodies.

TSLC1 expression is ubiquitous in normal adult tissues. However, in cultured tumor cells and in primary cancers which exhibit hypermethylation of the associated CpG island, TSLC1 expression is reduced or absent. For example, the expression of TSLC1 is absent in tumors with CpG island hypermethylation, including lung, colon, breast and brain tumors. This expression pattern is consistent with a tumor suppressor gene function for TSLC1.

Loss of heterozygosity on the long arm of chromosome 11 has been reported in NSCLC and other cancers (M. Iizuka et al., *Genes Chrom. Cancer* 13, 40 (1995); D. Rasio et al., *Cancer Res.* 55, 3988 (1995); and S. S. Wang et al., *Genes Chrom. Cancer* 25, 154 (1999)). Linkage studies of NSCLC are precluded because no hereditary forms are known (Y. Murakami et al., *Proc. Natl. Acad. Sci. USA*, 95, 8153 (1998); Y. Murakami et al., *Cancer Res.* 55, 3389 (1995); S. Thiagalingam et al., *Nature Genet.* 13, 343 (1996)). Several independent studies have suggested the presence of multiple tumor suppressor genes in this region, including the PPP2R1B gene at 11q23-24 (S. S. Wang et al., *Science* 282, 284 (1998).

In the present invention loss of heterozygosity (LOH) studies were combined with functional complementation of tumorigenicity by yeast artificial chromosomes (YACs) from normal chromosome 11 to localize the site of tumor suppressor activity within the 11q23-24 region. The suppression of tumorigenicity by this technique is considered to provide functional evidence of the presence of functional tumor suppressor genes in the segment of chromosome 11 inserted (H. Satoh et al., *Mol Carcinogen* 7, 157 (1993)).

The loss of heterozygosity study identified a 5cM commonly deleted region on 11q23 chromosome (M. Iizuka et al., supra). Transfer of overlapping YAC clones containing normal chromosome 11 into a human non-small cell lung cancer (NSCLC) cell line, A549, and murine LLC lung cancer cell lines were used to detect aberrations in function of tumor suppressor genes in chromosome 11 associated with NSCLC. By this method a potential tumor suppressor gene was localized to the central 700-kb fragment of y939b12, a 1.6 Mb YAC (6,9)(FIG. 1A). Then the tumor suppressor gene, TSLC1 (tumor suppressor in lung cancer 1, alias ST17), was further localized to a 100-kb candidate region of the YAC by the determination that cells transfected with truncated clones containing 1,100 kb of the parental YAC, but not those transfected with a 1,000 kb truncated derivative, showed strong suppressor activity.

Subsequent analysis of y939b12 identified a gene in the 100-kb candidate region containing TSLC1. A full length cDNA was constructed (as described in Example 1 herein) and found to be identical to a gene previously identified as belonging to the immunoglobulin superfamily and named IGSF4 by H. Gomyo et al., (*Genomics* 62, 139 (1999)). The gene structure was determined by comparison with genomic sequence, showing that TSLC1 spans more than 300-kb. The gene was rendered non-functional by deletion of 100 kb in the truncated YAC as discussed above. The TSLC1 gene encodes a putative membrane glycoprotein of 442 amino acids (GenBank Accession No. BAA75822) (SEQ ID NO:1). TSLC1, the encoded protein, has an extracellular domain containing 3 immunoglubulin-like C-2-type fragments, one transmembrane domain, and a short cytoplasmic domain similar to that of glycophorin C.

Since the predicted amino acid sequence of TSLC1 suggests that it is a transmembrane protein, the subcellular localization of TSLC1 was examined by expressing a TSLC1:gfp fusion protein in COS 7 cells, as described in Example 2 herein. TSLC1 localized in perinuclear and plasma membranes. The corresponding ΔTSLC1:gfp protein construct, lacking the signal peptide, was expressed in COS 7 cells, but failed to localize in plasma membrane. These findings together with the structural homology in the extracellular domains of TSLC1 to those of NCAM1, NCAM2 and other immunoglobulin superfamily proteins, suggest that TSLC1 might be involved in interaction of cells with other cells and/or the extracellular matrix.

Figure 1B:
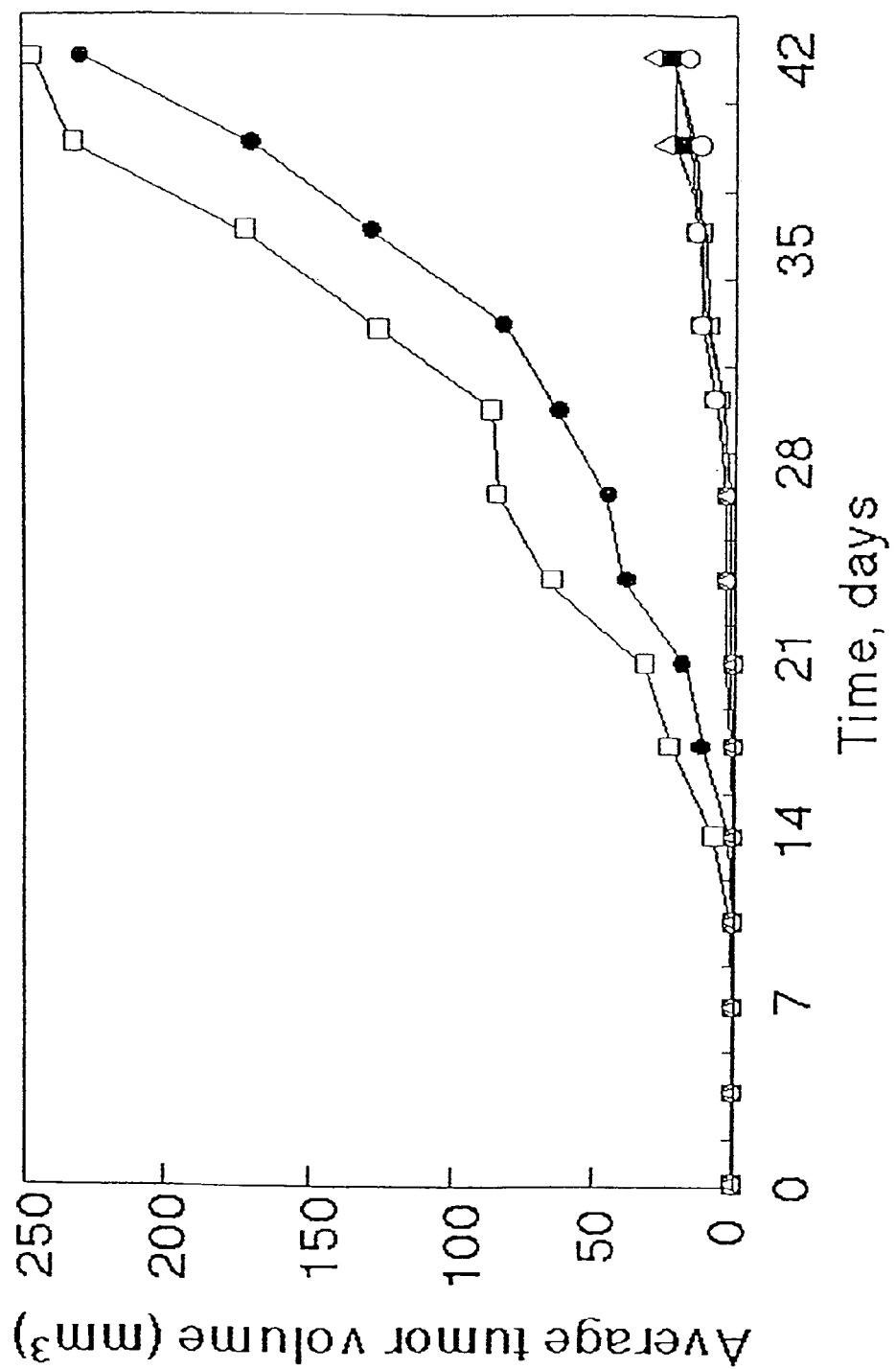
FIG. 1B is a graph showing the average volume of tumors that formed at eight sites as determined at the indicated times after injection of $10^5$ cells into live nude mice from the following A549 derivatives: A549 transfected with control plasmid (●); ATSLC1 (○), ATSLC2 (■), ATSLC3 (Δ), AΔTSLC (□).

Northern blot analysis of mRNAs obtained from a number of healthy tissues revealed the two expected TSLC1 transcripts of 4.4 kb and 1.6 kb (FIG. 1B). These mRNAs have been shown to express identical proteins (H. Gomyo et al., *Genomics* 62, 139 (1999). In contrast to the ubiquitous, high-level expression in most normal tissues, TSLC1 mRNA in A549 NSCLC cells was shown to be reduced to less than 15% of that seen in normal lung (Example 3). Analysis of eleven additional human lung adenocarcinoma cell lines (demonstrated that TSLC1 expression was absent from four of the eleven. A549 and all four of the cell lines lacking TSLC1 expression form tumors in nude mice. TSLC1 expression was also absent from 3 of 8 hepatocelluar carcinoma (HCC) cell lines and 8 of 11 pancreatic cancer (PAC) cell lines, suggesting that it may be involved in multiple human cancers (data not shown).

Transfected cell lines and a control A549 containing only plasmid DNA were examined for tumorigenicity by injecting $10^5$ cells subcutaneously into BALB/c athymic nu/nu mice (See FIG. 1B; Example 4). A549 and AΔTSLC1 cells both formed tumors at 8 of 8 sites of injection within 21 days (FIG. 1E). These tumors continued to grow until the experiment was terminated at 53 days. In contrast, only four of 24 injection sites of ATSLC1, 2 or 3 cell lines had palpable tumors at 21 days. Those tumors that eventually formed from ATSLC cells at 11 of 24 injection sites grew substantially slower than those of A549 to AΔTSLC1 cells. These results show that TSLC1 by itself has significant tumor suppressor activity.

Figure 2A:
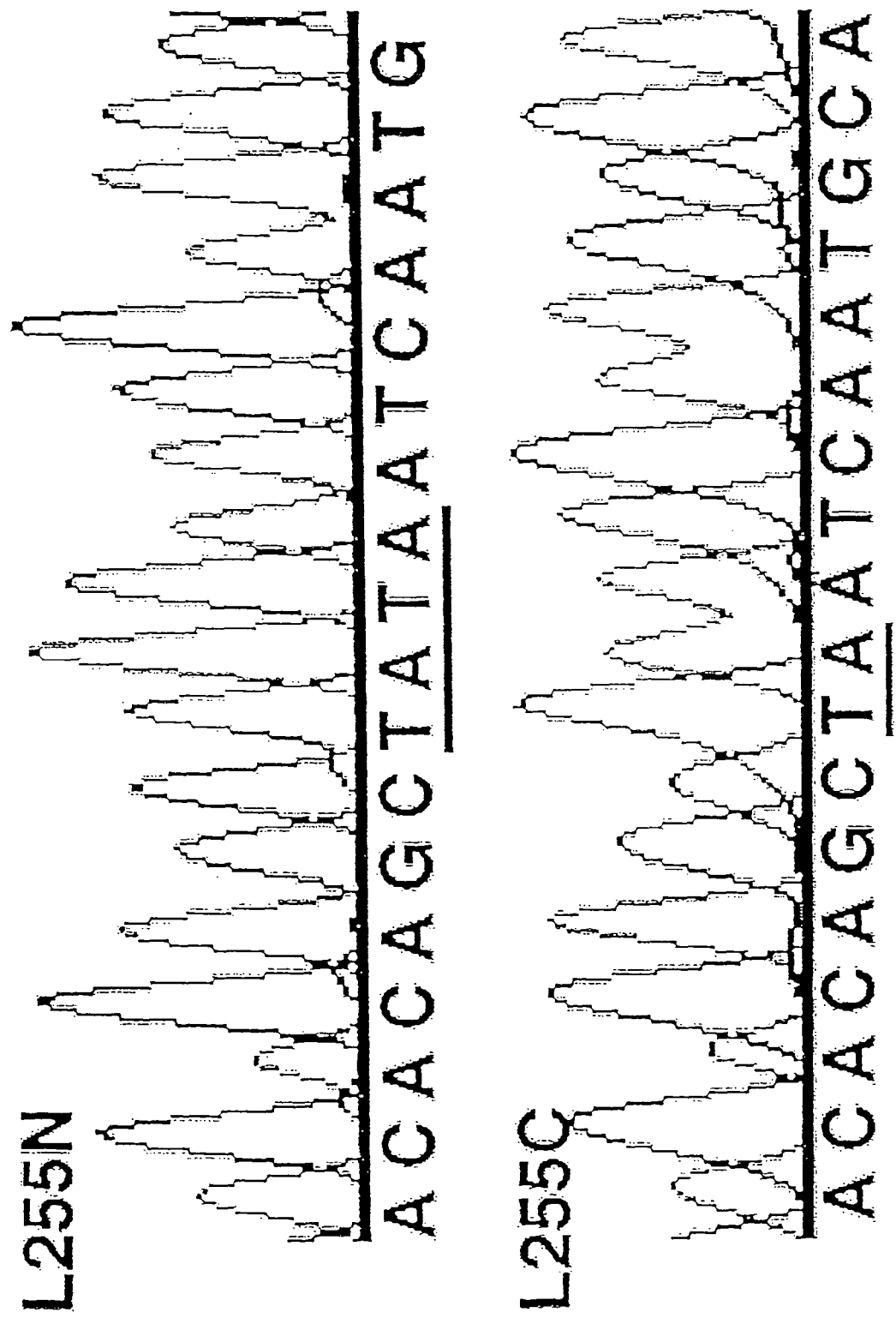
FIG. 2A shows a comparison the sequence of exon 10 of TSLC1 in L255N (SEQ ID NO:29) and L255C (SEQ ID NO:30) and identifies a 2 by deletion (underlined) in L255C.
Figure 2B:
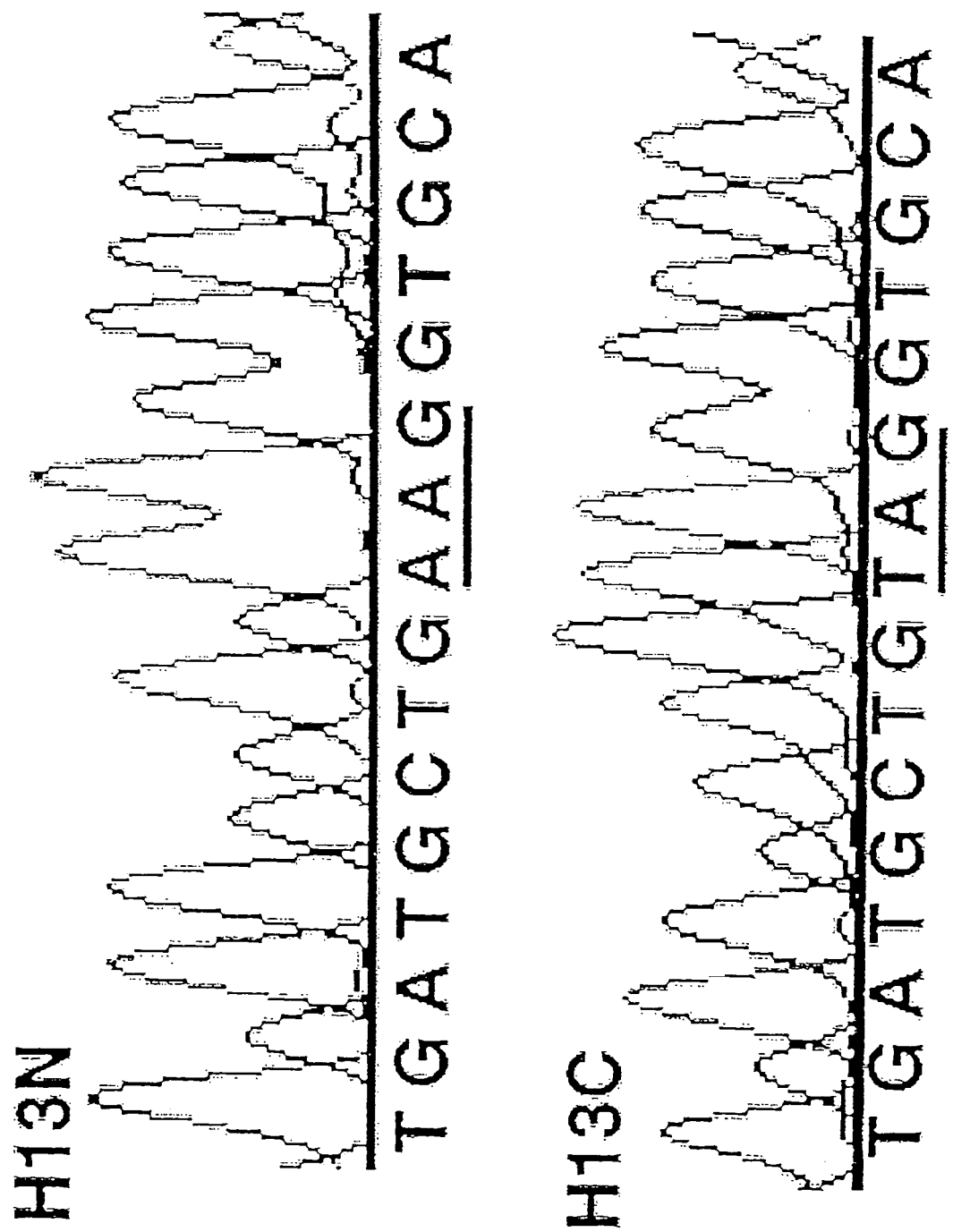
FIG. 2B shows a comparison of the sequence of exon 5 of TSLC1 in H13N (SEQ ID NO:31) and H13C (SEQ ID NO:32) and illustrates that codon 208 (underlined) is mutated in the TSLC1 gene in H13C.

To determine whether LOH in human NSCLC tumors uncovers a genetic alteration in the remaining TSLC1 allele, exons 1 to 10, together with their flanking sequences, were examined in 12 NSCLC cell lines and 54 primary NSCLC tumors using single strand conformation polymorphism (SSCP) analysis (Example 4). This analysis was also performed on 8 HCC cell lines, 36 primary HCCs, 11 pancreatic cancer cell lines and 40 primary cancers from exocrine pancreas. One of the NSCLC tumors showed a mobility shift accompanied by loss of wild-type fragment, while no alteration was observed in non-cancerous lung from the same patient. Sequence analysis revealed a 2-bp deletion in codons 243 to 244 of this tumor, resulting in a frameshift that is predicted to replace 19 amino acid residues at the COOH terminus of TSLC1 with a 52-residue sequence. (FIG. 2A). A nonsense mutation in codon 208 accompanied by loss of the wild-type allele was detected in one advanced HCC, H13C (FIG. 2C). A pancreatic cancer, PC22C, also carries a cancer specific mutation changing methionine to threonine at residue 383 in the transmembrane domain (data not shown).

Thus mutational inactivation of TSLC1 uncovered by LOH occurs in a small subset of primary human tumors. However, the remaining 158 tumor samples showed no evidence of sequence alteration in the TSLC1 gene, although LOH on 11 q23.2 was observed in 42%, 29% and 17% of primary NSCLC, HCC and PAC, respectively (Example 5).

Given the absence of structural alteration from most TSLC1 alleles uncovered by LOH, and reduction or absence of its expression in a number of tumorigenic cell lines, the possibility was examined that TSLC1 expression is down regulated through hypermethylation of the promoter, as observed in some other genes (T. Sakai et al., *Am J. Hum. Genet.* 48, 880 (1991); A Merlo et al, *Nature Med* 1, 686 (1995); and M. F. Kane et al., *Cancer Res.* 57, 808 (1997) 19-21). Determination of the nucleotide sequence in the region upstream from TSLC1 identified two CpG islands. Bisulfite sequencing was used to determine the methylation status of six CpG sites in a 93-bp fragment within a CpG island containing putative promoter sequences (Example 6). As shown in FIG. 3D, all cytosine residues in normal lung DNA were unmethylated and therefore were altered to thymine residues after bisulfite sequencing. In contrast, three of these CpG sites were methylated in the cell lines that showed complete loss of TSLC1 expression. In all, promoter sequences were methylated in 4 of 4 NSCLC cell lines with loss of TSLC1 expression but not methylated in 8 of 8 lines that essentially expressed TSLC1 (FIG. 3E). Thus, hypermethylation may act as the "second hit" to inactivate the TSLC1 allele in the significant fraction of NSCLC cell lines (and tumors) that have undergone LOH. It is interesting that methylation does not occur in the promoters of either A549 or A431. Both show very low, albeit clearly detectable TSLC1 mRNA levels. This suggests that further mechanisms regulating TSLC1 may be important in certain NSCLC.

Inhibition of tumor growth in inoperable patients is one of the important issues for the control of the disease. Loss of chromosome 11q23.2 occurs in about 40% of NSCLC, deleting one allele of TSLC1. Expression of tumor suppressor gene TSLC1 is further reduced or lost by mutational inactivation or promoter methylation in a significant fraction of NSCLC and also HCC and PAC cell lines. Although the A549 cell line, like advanced cancers, is known to carry multiple genetic alterations (Y. Murakami, T. Sekiya *Mutation Res.* 400, 421 (1998)), restoration of expression of this single gene was sufficient to significantly suppress the malignant phenotype of the cells. Therefore, TSLC1 and its effectors represent molecular targets for treatment of NSCLC and other human tumors.

The following are examples of specific embodiments for carrying out the present invention. The examples are offered for illustrative purposes only, and are not intended to limit the scope of the present invention in any way.

EXAMPLE 1

Functional mapping of tumor suppressor activity on 11q23.2 was accomplished by introduction of a 1.6 MB YAC and nested deletion derivatives of it into human NSCLS tumor cell line A549. Sixty-seven human ESTs from 11q23 (National Center for Biotechnology Information) were screened for tumor suppressor activity in A549 and an EST clone, SHGC-31226, was mapped within the 100 kb fragment identified on y939b12 (CITB) as responsible for essentially full repression of NSCLS tumor (See FIG. 1A). TSLC1 was localized to a 100 kb segment responsible essential for full suppression. A full-length cDNA was cloned based on cDNA sequencing, overlapping of expressed sequence tag (EST) sequences from the NCBI public database found on the worldwide web at ncbi.nlm.nih.gov/Entrez/, and 5' rapid amplification of cDNA ends (RACE) using the MARATHON® cDNA Amplification Kit (Clontech) according to the manufacturer's instructions. Olgonucleotide primers used for the first PCR reaction were as follows:

5'-CCATCCTAATACGACTCACTATAGGGC-3' (SEQ ID NO: 3)
and
5'-TCGCAACCTCTCCCTCGATCACTGTCA-3' (SEQ ID NO: 4)

and the primers used for the second PCR reaction were as follows:

5'-ACTCACTATAGGGCTCGAGCGGC-3' (SEQ ID NO: 5)
and
5'-AGAGCAACAGCAGAAGCCGGAGCCGGA-3' (SEQ ID NO: 6)

EXAMPLE 2

The subcellular localization of TSLC1 was examined by expressing a TSLC1:gfp fusion protein in COS 7 cells. A whole or a portion of coding sequences of TSLC1 were amplified by RT-PCR using adult human lung poly-A RNA (Clontech). The following primers used for amplification of TSLC1:

5'-GGGGTACCCAGGTGCCCGACATGGC-3' (SEQ ID NO:7) and
5'-AAGGAAAAAAGCGGCCGCCAGTTGGA-CACCTCATTGAA-3' (SEQ ID NO:8) The following primers were used for amplification of ΔTSLC1:

```
                                          (SEQ ID NO: 9)
5'-TTGGTACCCGAGCTCGGATCCTCCTGGTCCCACCACGT-3'
and (SEQ ID NO: 10)
5'-AAGGAAAAAAGCGGCCGCCAGTTGGACACCTCATTGAA-3'
```

Amplified fragments of TSLC1 and ΔTSLC1 were digested with restriction endonucleases, KpnI and NotI, subcloned into plasmid pcDNA3.1-Hygro (+) (Invitrogen) to yield plasmids pcTSLC1 and pcΔTSLC1, respectively. The inserts of pcTSLC1 and pcΔTSLC1 were then subcloned into plasmid pEGFP-N3 (Clontech), which contains a nucleotide encoding the green fluorescent peptide (gfp) to obtain plasmids pTSLC1-GFP and pΔTSLC1-GFP. COS 7 cells from RIKEN Cell Bank, Japan, were transfected with pTSLC1-GFP or pΔTSLC1-GFP and cultured on a cover slip. Cells were fixed with 2% paraformaldeyde 24 to 40 h after transfection and analyzed by fluorescence microscopy as described by K. Ghosh, H. P. Ghosh (*Biochem. Cell Biol.* 77, 165 (1999). The results of the fluorescence microscopy studies showed that TSLC1 localized in perinuclear and plasma membranes. The corresponding Δ TSLC1:gfp protein construct, lacking the signal peptide, was expressed but failed to localize in plasma membrane.

EXAMPLE 3

Levels of expression of TSLC1 in tumor cells were determined by measurement of mRNA in A549 cells. Human multiple tissue Northern blot and adult lung poly-A RNA were obtained from Clontech. Poly-A RNA from lung cancer cell lines and their derivatives was extracted using the FAST-TRACK® 2.0 kit (Invitrogen). PCR utilizing primers

```
5'-                                       (SEQ ID NO: 11)
CATCACAGTCCTGGTCCCACCACGTAATCT-3'
and 5'-                                       (SEQ ID NO: 12)
AATAGGGCCAGTTGGACACCTCATTGAAAC-3'
``` was used to derive TSLC1. Intensity of the signals was quantified using the BAS-2000 Imaging System (Fuji).

Northern Blot analysis of eleven additional human lung adenocarcinoma cell lines (Lane 1, A549; lane 2, ABC-1; lane 3, Calu-3; lane 4, NCI-H441; lane 5 NCI-H522; lane 6, LCMS; lane 7, LCOK; lane 8, VMRC-LCD; lane 9, PC-14; lane 10, SK-LU-1; lane 11, NCI-H596; lane 12, A431; lane 13, normal lung) showed that TSLC1 expression was absent from 4 of the 11 additional cell lines.

Similar Northern blot analysis found TSLC1 expression missing from 3 of 8 hepatocellular carcinoma cell lines (HCC) and 8 of 11 pancreatic cancer cell lines.

Expression of TSLC1 in various healthy tissues was studied by Northern blot analysis in healthy human heart; brain; placenta; lung; liver; skeletal muscle; kidney; and pancreas tissues. β-actin expression was used as a control. Strong expression of TSLC1 was found in healthy heart, brain, placenta and lung (lanes 1-4) with moderate expression in skeletal muscle, kidney, and pancreas (lanes 6-8).

The study was repeated in several NSCLC lines using Northern blot analysis of TSLC1 mRNA, with normal lung and β-actin as controls. TSLC1 mRNA was present in ABC-1, NCI-H522 and VMRC-LCD cell lines and in normal lung, but was reduced or absent in several other NSCLC cell lines. Expression was completely absent in PC-14, SK-LU-1, and NCI-H596 cell lines (lanes 9-11).

EXAMPLE 4

To determine whether LOH in human NSCLC tumors uncovers a genetic alteration in the remaining TSLC1 allele, exons 1 to 10, together with their flanking sequences, were examined in 12 NSCLC cell lines and 54 primary NSCLC tumors using single strand conformation polymorphism (SSCP) analysis. Primary tumors were supplied by Pathology Division, National Cancer Center Research Institute and Japan Research Group of Pancreatic Cancer. All the experiments using human materials were performed in accordance with the institutional guidelines. Genomic DNA was extracted by Proteinase K-phenol-chloroform extraction method. PCR-SSCP analysis was essentially carried out using a method as described previously by M. Orita et al. (*Genomics* 5, 874 (1989)), which is incorporated herein by reference in its entirety.

Primer pairs used for amplification of exon 5 of TSLC1 were as follows:

```
5'-CACCCAACTCTGGTGTCTTGGTAC-3'    (SEQ ID NO: 13)
and

5'-CTCTACGCCCTCAGAATAAGATAC-3'.   (SEQ ID NO: 14)
```

Primer pairs used for amplification of exon 10 of TSLC1 were as follows:

```
5'-TTACACAGAGGCCATCAGACAGTC-3'    (SEQ ID NO: 15)
and

5'-AAATAGGGCCAGTTGGACACCTC-3'.    (SEQ ID NO: 16)
```

Amplification products were denatured at 95° C. for 3 min and separated on 5% polyacrylamide gels with buffer containing 2-[N-morpholino]ethanesulfonic acid as described in Y. Kukita et al. (*Hum. Mutation* 10, 400 (1997). SSCP analysis of exons 5 and 10 of TSLC1 in cell lines L213N, L255C, L255N, L213N, H13C and H13N showed loss of the wild type allele and mobility shift in the remaining allele in L255C and H13C. One NSCLC tumor showed a mobility shift accompanied by loss of wild-type fragment, while no alteration was observed in non-cancerous lung from the same patient.

DNA fragments were eluted from gels, amplified, and sequenced by the ABI PRISM® dye terminator cycle sequencing ready reaction kit (Perkin-Elmer) using an ABI 377 DNA auto-sequencer (Applied Biosystems). Sequence analysis revealed a 2-bp deletion in codons 243 to 244 of this tumor, resulting in a frameshift that is predicted to replace 19 amino acid residues at the COOH terminus of TSLC1 with a 52-residue sequence.

EXAMPLE 5

Human multiple tissue Northern blot and adult lung poly-A RNA were obtained from Clontech. Poly-A RNA from lung cancer cell lines and their derivatives was extracted using the FASTTRACK® 2.0 kit (Invitrogen). A 961-bp PCR-derived fragment of SEQ ID NO:17 (nt 411-1,371 of TSLC1 cDNA) obtained using primers

```
5'-                                         (SEQ ID NO: 18)
CATCACAGTCCTGGTCCCACCACGTAATCT-3'
and 5'-                                         (SEQ ID NO: 19)
AATAGGGCCAGTTGGACACCTCATTGAAAC-3'
``` was used as a probe for detection of TSLC1 in lung cancer cell lines. Intensity of the signals was quantified using the BAS-2000 (Fuji Imaging System).

EXAMPLE 6

To examine tumor suppressor activity of the TSLC1 gene, mini-genes were constructed that carry the complete coding sequence of TSLC1 or a truncated version lacking the NH2-terminal signal peptide (ATSLC1). TSLC1 expression was restored by transfection of mini-genes into A549. Plasmids pcTSLC1, pcΔTSLC1 and pcDNA3.1-Hygro(+) were transfected into A549 cells using LIPOFECTAMINE PLUS® (GIBCO BRL) and hygromycin resistant cells were cloned to derive three independent lines containing full length TSLC1 (ATSLC1, 2, 3) and one cell line with the truncated mini-gene (AΔTSLC1). Northern blot analysis showed relative levels of TSLC1 transcripts of 4.4 kb and 1.6 kb, transcripts from full length (TSLC1, 1.8 kb) and truncated (ΔTSLC1, 1.4 kb) mini-genes, and β-actin (as control). These results showed that the mini-genes encoding full length TSLC1 restored TSLC1 mRNA levels in A549 from 15% of that observed in normal lung tissue to levels 120%, 660% and 100% of that observed in normal lung tissue in ATSLC1, 2, and 3, respectively. AΔTSLC1 expressed the truncated message at levels similar to ATSLC1 and 3. As reported above, in AΔTSLC1 this message is translated but the resulting protein does not localize to the cell membrane. This result indicates that the tumor suppressor activity of TSLC1 depends upon localization of the encoded protein to the cell membrane.

EXAMPLE 7

Transfected cell lines AΔTSLC1, 2 and 3 (which each contain a promoter plus a TSLC1 cDNA that lacks the N-terminal signal sequences) and a control A549 containing only plasmid DNA were examined for tumorigenicity by injecting cells of each subcutaneously into BALB/c athymic nu/nu mice. A suspension of 1×10⁵ cells in 0.2 ml PBS was injected subcutaneously into one to four sites on the flanks of 5- to 6-week old female BALB/c athymic nu/nu mice (Charles River). Tumor growth was assessed by measuring the xenografts in three dimensions. All animal experiments were performed in accordance with the institutional guidelines.

In these experiments A549 and AΔTSLC1 cells both formed tumors at 8 of 8 sites of injection within 21 days (FIG. 1E). These tumors continued to grow until the experiment was terminated at 53 days. In contrast, only four of 24 injection sites of ATSLC1, 2, or 3 cell lines (which contain a promoter plus a full length TSLC1 cDNA) had palpable tumors at 21 days. Those tumors that eventually formed from ATSLC cells at 11 of 24 injection sites grew substantially slower than those of A549 or AΔTSLC1 cells. These experiments show that TSLC1 by itself has significant tumor suppressor activity.

EXAMPLE 8

DNA fragments containing four polymorphic STS markers, D11S4111, D11S1235, D11S2077 and D11S1885, were amplified by PCR from NSCLC, HCC and PAC tumors and non-cancerous tissues of the same patients using pairs of primers, one of which was labeled with $^{32}$P-dCTP. Amplified fragments were subjected to electrophoresis in polyacrylamide gels containing 7M Urea and autoradiography. Loss of heterozygosity on 11q23.2 was observed in 42%, 29% and 17% of primary HSCLC, HCC AND PAC, respectively.

EXAMPLE 9

To determine whether TSLC1 is down regulated through hypermethylation of the promoter, the nucleotide sequence in the region upstream from TSLC1 was examined to identify two CpG islands. Bisulfite sequence was used to determine the methylation status of six CpG sites in a 93-bp fragment within a CpG island containing putative promoter sequences as described by M. Frommer et al. (*Proc. Natl. Acad. Sci. USA* 89, 1827 (1992). After denaturing with NaOH (0.3M), genomic DNA (2 μg) was incubated with sodium bisulfite (3.1 M; Sigma) and hydroquinone (0.8 mM; Sigma) pH 5.0, at 55° C. for 20 h, purified and treated with NaOH (0.2 M) for 10 min at 37° C. Modified DNA (100 ng) was subjected to PCR to amplify the promoter sequence of TSLC1 with the following primers:

```
5'-                                         (SEQ ID NO: 20)
GTGAGTGACGGAAATTTGTAATGTTTGGTT-3'
and 5'-                                         (SEQ ID NO: 21)
AATCTAACTTCTTATACACCTTTATTAAAA-3'.
```

Figure 2D:
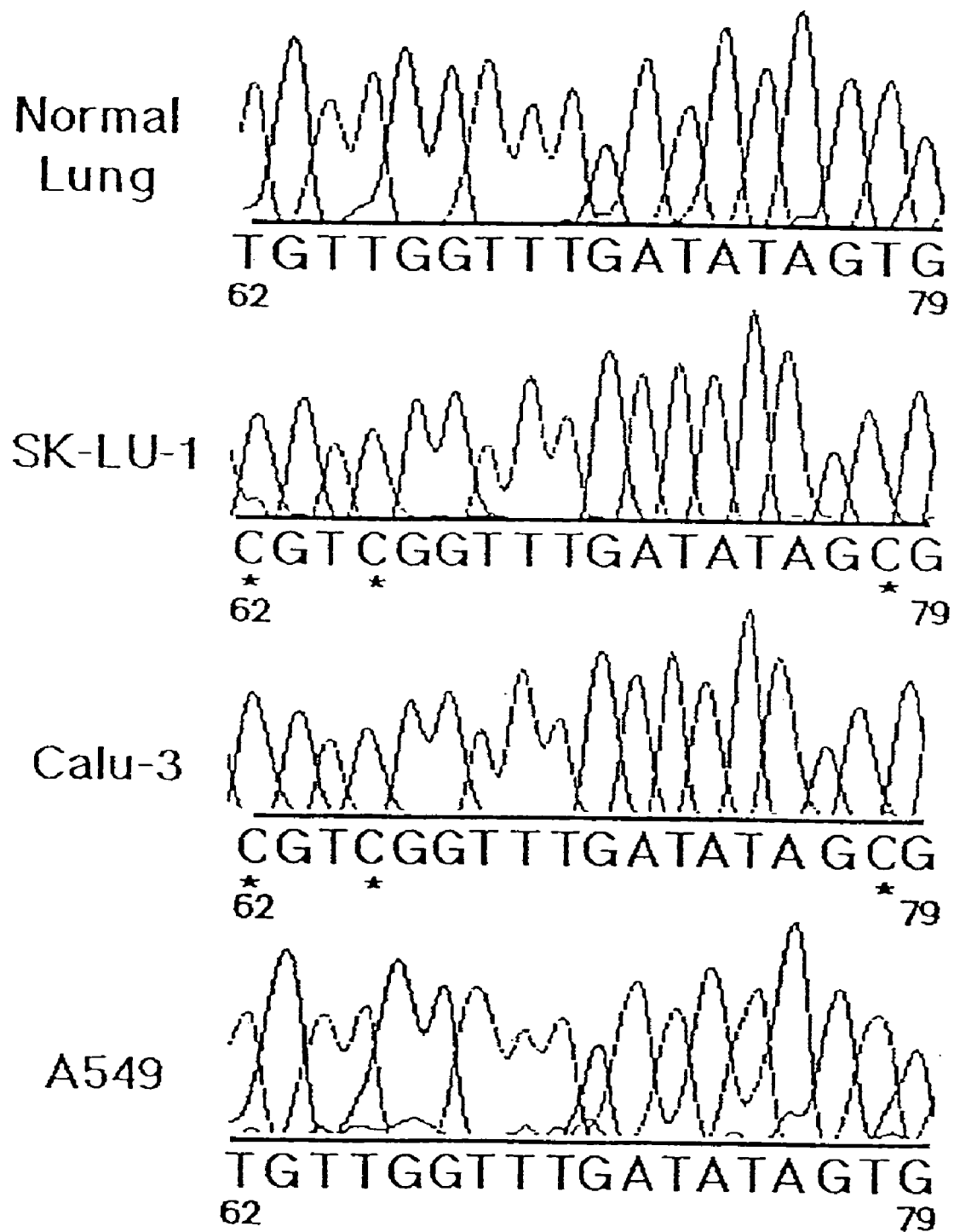
FIG. 2D shows residues 62-79 bp of the 93-bp fragment of the CpG island in normal lung, (SEQ ID NO:25), SK-LU-1 (SEQ ID NO:26), Calu-3 (SEQ ID NO:27), and A549 (SEQ ID NO:28). Bisulfite sequencing identified three methylated cytosine residues in SK-LU-1 and Calu-3 cell lines, but not in A549 or normal lung. Asterisks indicate the nucleotides corresponding to methylated cytosine residues at CpG sites.

The PCR products were purified and directly sequenced to obtain average methylation levels. PCR products containing bisulfite-resistant cytosines were subcloned and at least 6 clones were sequenced for confirmation (FIGS. 2D and 2E).

EXAMPLE 10

Bisulfite sequencing was used to determine the methylation status of six CpG sites in a 93-bp fragment within a CpG island containing putative promoter sequences. Bisulfite sequencing was performed as described (M. Frommer et al., *Proc. Natl. Acad. Sci. USA* 89, 1827 (1992)). After denaturing with NaOH (0.3M), genomic DNA (2 μg) was incubated with sodium bisulfite (3.1 M; Sigma) and hydroquinone (0.8 mM; Sigma) pH 5.0, at 55° C. for 20 h, purified and treated with NaOH (0.2 M) for 10 min at 37° C. Modified DNA (100 ng) was subjected to PCR to amplify the promoter sequence of TSLC1 with the following primers:

```
5'-                                         (SEQ ID NO: 22
GTGAGTGACGGAAATTTGTAATGTTTGGTT-3'
and 5'-                                         (SEQ ID NO: 23)
AATCTAACTTCTTATACACCTTTATTAAAA-3'.
```

The PCR products were purified and directly sequenced to obtain average methylation levels. PCR products containing bisulfite-resistant cytosines were subcloned and at least 6 clones were sequenced for confirmation. The results of these studies are shown in FIGS. 2A-E.

It will be apparent to those skilled in the art that various changes may be made in the invention without departing from the spirit and scope thereof, and therefore, the invention encompasses embodiments in addition to those specifically disclosed in the specification, but only as indicated in the appended claims.

What is claimed is:

1. A method of determining whether a subject has a cell proliferative disorder associated with tumor suppressor lung cancer 1 (TSLC1) comprising contacting a nucleic acid sample from the subject with a reagent that detects the level of TSLC1 polynucleotide and determining the level of the TSLC1 polynucleotide as compared with the level in a comparable healthy cell, wherein a difference in the level of the TSLC1 polynucleotide between the sample from the subject and the healthy cell is indicative of a proliferative disorder in the subject, wherein the nucleic acid is DNA, and wherein the level of TSLC1 polynucleotide is determined by methylation specific PCR.

2. The method of claim 1, wherein the nucleic acid encodes the TSLC1.

3. The method of claim 1, wherein the reagent is a nucleic acid probe or primer that binds to the TSLC1 polynucleotide.

4. The method of claim 1, wherein the sample comprises a cancer cell.

5. The method of claim 4, wherein the cancer cell is a lung cancer cell.

6. The method of claim 5, wherein the lung cancer cell is a human non-small cell lung cancer cell.

7. The method of claim 4, wherein the cancer cell is a liver cancer cell.

8. The method of claim 7, wherein the liver cancer cell is a hepatocellular carcinoma cell.

9. A method of detecting a cell proliferative disorder associated with tumor suppressor lung cancer 1 (TSLC1) in a subject comprising contacting a cell component of a proliferating cell of the subject with a primer pair that detects the level of the cell component in the proliferating cell and determining a modification in the level of the cell component in the proliferating cell as compared with a comparable healthy cell, wherein the cell component indicates the level of TSLC1 in the cell and the modification indicates the disorder associated with TSLC1, wherein the modification is a decrease in the level of TSLC1, wherein the cell component is DNA, and wherein the wherein the level of TSLC1 polynucleotide is determined by methylation specific PCR.

10. The method of claim 9, wherein the proliferating cell is a cancer cell.

11. The method of claim 10, wherein the cancer cell is a lung cancer cell.

12. The method of claim 11, wherein the lung cancer cell is a human non-small cell lung cancer cell.

13. The method of claim 10, wherein the cancer cell is a liver cancer cell.

14. The method of claim 13, wherein the liver cancer cell is a hepatocellular carcinoma cell.

15. The method of claim 3, wherein the nucleic acid probe or primer has a detectable label.

16. The method of claim 9, wherein the primer pair is detectably labeled.

17. The method of claim 1, wherein subject has loss of heterozygosity of 11q23 chromosome.

18. The method of claim 9, wherein subject has loss of heterozygosity of 11q23 chromosome.

* * * * *

```
                            SEQUENCE LISTING

<160> NUMBER OF SEQ ID NOS: 32

<210> SEQ ID NO 1
<211> LENGTH: 442
<212> TYPE: PRT
<213> ORGANISM: Homo sapiens

<400> SEQUENCE: 1

Met Ala Ser Val Val Leu Pro Ser Gly Ser Gln Cys Ala Ala Ala
1               5                   10                  15

Ala Ala Ala Ala Pro Pro Gly Leu Arg Leu Arg Leu Leu Leu Leu
                20                  25                  30

Phe Ser Ala Ala Ala Leu Ile Pro Thr Gly Asp Gly Gln Asn Leu Phe
            35                  40                  45

Thr Lys Asp Val Thr Val Ile Glu Gly Glu Val Ala Thr Ile Ser Cys
    50                  55                  60

Gln Val Asn Lys Ser Asp Asp Ser Val Ile Gln Leu Leu Asn Pro Asn
65                  70                  75                  80

Arg Gln Thr Ile Tyr Phe Arg Asp Phe Arg Pro Leu Lys Asp Ser Arg
                85                  90                  95

Phe Gln Leu Leu Asn Phe Ser Ser Glu Leu Lys Val Ser Leu Thr
            100                 105                 110

Asn Val Ser Ile Ser Asp Glu Gly Arg Tyr Phe Cys Gln Leu Tyr Thr
            115                 120                 125

Asp Pro Pro Gln Glu Ser Tyr Thr Thr Ile Thr Val Leu Val Pro Pro
        130                 135                 140

Arg Asn Leu Met Ile Asp Ile Gln Lys Asp Thr Ala Val Glu Gly Glu
145                 150                 155                 160

Glu Ile Glu Val Asn Cys Thr Ala Met Ala Ser Lys Pro Ala Thr Thr
                165                 170                 175

Ile Arg Trp Phe Lys Gly Asn Thr Glu Leu Lys Gly Lys Ser Glu Val
            180                 185                 190

Glu Glu Trp Ser Asp Met Tyr Thr Val Thr Ser Gln Leu Met Leu Lys
        195                 200                 205

Val His Lys Glu Asp Asp Gly Val Pro Val Ile Cys Gln Val Glu His
    210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
                245                 250                 255

Thr Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met Pro
        275                 280                 285

Gln His Ala Val Leu Ser Gly Pro Asn Leu Phe Ile Asn Asn Leu Asn
    290                 295                 300

Lys Thr Asp Asn Gly Thr Tyr Arg Cys Glu Ala Ser Asn Ile Val Gly
305                 310                 315                 320

Lys Ala His Ser Asp Tyr Met Leu Tyr Val Tyr Asp Pro Pro Thr Thr
                325                 330                 335
```

```
Ile Pro Pro Pro Thr Thr Thr Thr Thr Thr Thr Thr Thr Thr
            340                 345                 350

Thr Ile Leu Thr Ile Ile Thr Asp Ser Arg Ala Gly Glu Glu Gly Ser
        355                 360                 365

Ile Arg Ala Val Asp His Ala Val Ile Gly Gly Val Val Ala Val
    370                 375                 380

Val Phe Ala Met Leu Cys Leu Leu Ile Ile Leu Gly Arg Tyr Phe Ala
385                 390                 395                 400

Arg His Lys Gly Thr Tyr Phe Thr His Glu Ala Lys Gly Ala Asp Asp
                405                 410                 415

Ala Ala Asp Ala Asp Thr Ala Ile Ile Asn Ala Glu Gly Gly Gln Asn
                420                 425                 430

Asn Ser Glu Glu Lys Lys Glu Tyr Phe Ile
                435                 440

<210> SEQ ID NO 2
<211> LENGTH: 1329
<212> TYPE: DNA
<213> ORGANISM: Homo sapiens
<220> FEATURE:
<221> NAME/KEY: misc_feature
<222> LOCATION: (1)..(1329)
<223> OTHER INFORMATION: n is any nucleotide

<400> SEQUENCE: 2
tatcgcagag gttaagntgg agtggtgcnt ttggaacccc cggatcccccc tttgtctcac     60 ccacccgnt ntnttnttcc aattgttttn tccccttntg ngcntgnaac cgagttnggg    120
ntgatgatgn ccataaagca agttgccatc tctgtaccac tttacacaga ggccatcaga    180
cagtcacggt gctttacccc ttcatctttc aggtacatac ttcactcatg aagccaaagg    240
agccgatgac gcagcagacg cagacacagc tataatcaat gcagaaggag gacagaacaa    300
ctccgaagaa aagaaagagt acttcatcta gatcagcctt tttgtttcaa tgaggtgtcc    360
aactggccct atttagatga taaagagaca gtgatattgg aacttgcgag aaattcgtgt    420 gttttttttat gaatgggtgg aaaggtgtga gactgggaag gcttgggatt tgctgtgtaa    480
aaaaaaaaaa aaaatgttct ttggaaagta cactctgctg tttgacacct cttttttcgt    540
ttgtttgttt gtttaatttt tatttctncc taccaagtca aacttggata cttggattta    600
gtttcagtag attgcagaaa attctgtgcc ttgttttttg tttgtttgtt gcgtncctt    660 cttttccccc tttgtgcaca tttatttcct ccctctaccc caatttcgga ttttttccaa    720
aatctcccat tttggaattt gcctgctggg attccttaga ctcttttcct tcccttttct    780
gttctagttt tttactttg tttatttta tggtaactgc tttctgttcc aaattcagtt    840
tcataaaagg agaaccagca cagcttagat ttcatagttc agaatttagt gtatccataa    900
tgcattcttc tctgttgtcg taaagatttg ggtgaacaaa caatgaaaac tctttgctgc    960
tgcccatgtt tcaaatactt agagcagtga agactagaaa attagactgt gattcagaaa   1020
atgttctgtt tgctgtggaa ctacattact gtacagggtt atctgcaagt gaggtgtgtc   1080
acaatgagat tgaatttcac tgtctttaat tctgtatctg tagacggctc agtatagata   1140
ccctacgctg tccagaaagg tttggggcag aaaggactcc tccttttcc atgccctaaa   1200 cagacctgac aggtgaggtc tgttcctttt atataagtgg acaaattttg agttgccaca   1260 ggagggaag tagggagggg ggaaatacag ttctgctctg gttgtttctg ttccaaatga   1320
ttccatcca                                                          1329
```

<210> SEQ ID NO 3
<211> LENGTH: 27
<212> TYPE: DNA
<213> ORGANISM: Artificial sequence
<220> FEATURE:
<223> OTHER INFORMATION: Primer for PCR

<400> SEQUENCE: 3
ccatcctaat acgactcact atagggc                                27

<210> SEQ ID NO 4
<211> LENGTH: 27
<212> TYPE: DNA
<213> ORGANISM: Artificial sequence
<220> FEATURE:
<223> OTHER INFORMATION: Primer for PCR

<400> SEQUENCE: 4
tcgcaacctc tccctcgatc actgtca                                27

<210> SEQ ID NO 5
<211> LENGTH: 23
<212> TYPE: DNA
<213> ORGANISM: Artificial sequence
<220> FEATURE:
<223> OTHER INFORMATION: Primer for PCR

<400> SEQUENCE: 5
actcactata gggctcgagc ggc                                    23

<210> SEQ ID NO 6
<211> LENGTH: 27
<212> TYPE: DNA
<213> ORGANISM: Artificial sequence
<220> FEATURE:
<223> OTHER INFORMATION: Primer for PCR

<400> SEQUENCE: 6
agagcaacag cagaagccgg agccgga                                27

<210> SEQ ID NO 7
<211> LENGTH: 25
<212> TYPE: DNA
<213> ORGANISM: Artificial sequence
<220> FEATURE:
<223> OTHER INFORMATION: Primer for PCR

<400> SEQUENCE: 7
ggggtaccca ggtgcccgac atggc                                  25

<210> SEQ ID NO 8
<211> LENGTH: 38
<212> TYPE: DNA
<213> ORGANISM: Artificial sequence
<220> FEATURE:
<223> OTHER INFORMATION: Primer for PCR

<400> SEQUENCE: 8
aaggaaaaaa gcggccgcca gttggacacc tcattgaa                    38

<210> SEQ ID NO 9
<211> LENGTH: 38
<212> TYPE: DNA
<213> ORGANISM: Artificial sequence
<220> FEATURE:

<223> OTHER INFORMATION: Primer for PCR

<400> SEQUENCE: 9
ttggtacccg agctcggatc ctcctggtcc caccacgt           38

<210> SEQ ID NO 10
<211> LENGTH: 38
<212> TYPE: DNA
<213> ORGANISM: Artificial sequence
<220> FEATURE:
<223> OTHER INFORMATION: Primer for PCR

<400> SEQUENCE: 10
aaggaaaaaa gcggccgcca gttggacacc tcattgaa           38

<210> SEQ ID NO 11
<211> LENGTH: 30
<212> TYPE: DNA
<213> ORGANISM: Artificial sequence
<220> FEATURE:
<223> OTHER INFORMATION: PCR utilizing primer

<400> SEQUENCE: 11
catcacagtc ctggtcccac cacgtaatct                    30

<210> SEQ ID NO 12
<211> LENGTH: 30
<212> TYPE: DNA
<213> ORGANISM: Artificial sequence
<220> FEATURE:
<223> OTHER INFORMATION: PCR utilizing primer

<400> SEQUENCE: 12
aatagggcca gttggacacc tcattgaaac                    30

<210> SEQ ID NO 13
<211> LENGTH: 24
<212> TYPE: DNA
<213> ORGANISM: Artificial sequence
<220> FEATURE:
<223> OTHER INFORMATION: Primer for PCR

<400> SEQUENCE: 13
cacccaactc tggtgtcttg gtac                          24

<210> SEQ ID NO 14
<211> LENGTH: 24
<212> TYPE: DNA
<213> ORGANISM: Artificial sequence
<220> FEATURE:
<223> OTHER INFORMATION: Primer for PCR

<400> SEQUENCE: 14
ctctacgccc tcagaataag atac                          24

<210> SEQ ID NO 15
<211> LENGTH: 24
<212> TYPE: DNA
<213> ORGANISM: Artificial sequence
<220> FEATURE:
<223> OTHER INFORMATION: Primer for PCR

<400> SEQUENCE: 15
ttacacagag gccatcagac agtc                          24

```
<210> SEQ ID NO 16
<211> LENGTH: 23
<212> TYPE: DNA
<213> ORGANISM: Artificial sequence
<220> FEATURE:
<223> OTHER INFORMATION: Primer for PCR

<400> SEQUENCE: 16
aaatagggcc agttggacac ctc                                            23

<210> SEQ ID NO 17
<211> LENGTH: 961
<212> TYPE: DNA
<213> ORGANISM: Homo sapiens
<220> FEATURE:
<221> NAME/KEY: misc_feature
<222> LOCATION: (1)..(961)
<223> OTHER INFORMATION: n is any nucleotide

<400> SEQUENCE: 17
gacagtgata ttggaacttg cgagaaattc gtgtgttttt ttatgaatgg gtggaaaggt     60
gtgagactgg gaaggcttgg gatttgctgt gtaaaaaaaa aaaaaaaatg ttctttggaa    120
agtacactct gctgtttgac acctcttttt tcgtttgttt gtttgtttaa ttttttatttc   180 tncctaccaa gtcaaacttg gatacttgga tttagtttca gtagattgca gaaaattctg   240
tgccttgttt tttgtttgtt tgttgcgtnc ctttcttttc ccctttgtg cacatttatt    300 tcctccctct accccaattt cggattttt ccaaaatctc ccattttgga atttgcctgc    360
tgggattcct tagactcttt tccttccctt ttctgttcta gttttttact tttgtttatt   420
tttatggtaa ctgctttctg ttccaaattc agtttcataa aaggagaacc agcacagctt   480
agatttcata gttcagaatt tagtgtatcc ataatgcatt cttctctgtt gtcgtaaaga   540
tttgggtgaa caaacaatga aaactctttg ctgctgccca tgtttcaaat acttagagca   600
gtgaagacta gaaaattaga ctgtgattca gaaaatgttc tgtttgctgt ggaactacat   660
tactgtacag ggttatctgc aagtgaggtg tgtcacaatg agattgaatt tcactgtctt   720
taattctgta tctgtagacg gctcagtata gatacccta c gctgtccaga aaggtttggg   780
gcagaaagga ctcctccttt ttccatgccc taaacagacc tgacaggtga ggtctgttcc   840
ttttatataa gtggacaaat tttgagttgc cacaggaggg gaagtaggga gggggaaat    900 acagttctgc tctggttgtt tctgttccaa atgattccat ccacctttcc caatcggcct   960
t                                                                   961

<210> SEQ ID NO 18
<211> LENGTH: 30
<212> TYPE: DNA
<213> ORGANISM: Artificial sequence
<220> FEATURE:
<223> OTHER INFORMATION: Primer for PCR

<400> SEQUENCE: 18
catcacagtc ctggtcccac cacgtaatct                                     30

<210> SEQ ID NO 19
<211> LENGTH: 30
<212> TYPE: DNA
<213> ORGANISM: Artificial sequence
<220> FEATURE:
<223> OTHER INFORMATION: Primer for PCR

<400> SEQUENCE: 19
```
aatagggcca gttggacacc tcattgaaac                                    30

<210> SEQ ID NO 20
<211> LENGTH: 30
<212> TYPE: DNA
<213> ORGANISM: Artificial sequence
<220> FEATURE:
<223> OTHER INFORMATION: Primer for PCR

<400> SEQUENCE: 20
gtgagtgacg gaaatttgta atgtttggtt                                    30

<210> SEQ ID NO 21
<211> LENGTH: 30
<212> TYPE: DNA
<213> ORGANISM: Artificial sequence
<220> FEATURE:
<223> OTHER INFORMATION: Primer for PCR

<400> SEQUENCE: 21
aatctaactt cttatacacc tttattaaaa                                    30

<210> SEQ ID NO 22
<211> LENGTH: 30
<212> TYPE: DNA
<213> ORGANISM: Artificial sequence
<220> FEATURE:
<223> OTHER INFORMATION: Primer for PCR

<400> SEQUENCE: 22
gtgagtgacg gaaatttgta atgtttggtt                                    30

<210> SEQ ID NO 23
<211> LENGTH: 30
<212> TYPE: DNA
<213> ORGANISM: Artificial sequence
<220> FEATURE:
<223> OTHER INFORMATION: Primer for PCR

<400> SEQUENCE: 23
aatctaactt cttatacacc tttattaaaa                                    30

<210> SEQ ID NO 24
<211> LENGTH: 153
<212> TYPE: DNA
<213> ORGANISM: Homo sapiens

<400> SEQUENCE: 24
gtgagtgacg gaaatttgca acgtctggtt cgctaggcca gatgcactcg gtgtgcggga    60
cagaggaccc tcttaaggga gattctccag tcgtcggtct gatacagcga ttgctataaa   120
cattcctaat aaaggtgtac aagaagctag acc                                153

<210> SEQ ID NO 25
<211> LENGTH: 18
<212> TYPE: DNA
<213> ORGANISM: Homo sapiens

<400> SEQUENCE: 25
tgttggtttg atatagtg                                                 18

<210> SEQ ID NO 26
<211> LENGTH: 18
<212> TYPE: DNA
<213> ORGANISM: Homo sapiens

```
<400> SEQUENCE: 26
cgtcggtttg atatagcg                                              18

<210> SEQ ID NO 27
<211> LENGTH: 18
<212> TYPE: DNA
<213> ORGANISM: Homo sapiens

<400> SEQUENCE: 27
cgtcggtttg atatagcg                                              18

<210> SEQ ID NO 28
<211> LENGTH: 18
<212> TYPE: DNA
<213> ORGANISM: Homo sapiens

<400> SEQUENCE: 28
tgttggtttg atatagtg                                              18

<210> SEQ ID NO 29
<211> LENGTH: 18
<212> TYPE: DNA
<213> ORGANISM: Homo sapiens

<400> SEQUENCE: 29
acacagctat aatcaatg                                              18

<210> SEQ ID NO 30
<211> LENGTH: 18
<212> TYPE: DNA
<213> ORGANISM: Homo sapiens

<400> SEQUENCE: 30
acacagctaa tcaatgca                                              18

<210> SEQ ID NO 31
<211> LENGTH: 16
<212> TYPE: DNA
<213> ORGANISM: Homo sapiens

<400> SEQUENCE: 31
tgatgctgaa ggtgca                                                16

<210> SEQ ID NO 32
<211> LENGTH: 16
<212> TYPE: DNA
<213> ORGANISM: Homo sapiens

<400> SEQUENCE: 32
tgatgctgta ggtgca                                                16
```